United States Patent
Kyriakou

(10) Patent No.: US 11,398,031 B2
(45) Date of Patent: Jul. 26, 2022

(54) METHOD FOR AUTOMATICALLY DETERMINING A WEIGHTING FOR A ROADMAP METHOD, COMPUTER PROGRAM, DATA MEMORY AND CORRESPONDING IMAGING APPARATUS

(71) Applicant: Siemens Healthcare GmbH, Erlangen (DE)

(72) Inventor: Yiannis Kyriakou, Spardorf (DE)

(73) Assignee: Siemens Healthcare GmbH, Erlangen (DE)

( * ) Notice: Subject to any disclaimer, the term of this patent is extended or adjusted under 35 U.S.C. 154(b) by 309 days.

(21) Appl. No.: 16/502,301

(22) Filed: Jul. 3, 2019

(65) Prior Publication Data
US 2020/0020100 A1 Jan. 16, 2020

(30) Foreign Application Priority Data
Jul. 11, 2018 (DE) .................... 10 2018 211 477.3

(51) Int. Cl.
*G06T 7/00* (2017.01)
*G16H 30/40* (2018.01)
(Continued)

(52) U.S. Cl.
CPC .............. *G06T 7/0014* (2013.01); *G06T 7/11* (2017.01); *G06T 7/344* (2017.01); *G16H 30/40* (2018.01);
(Continued)

(58) Field of Classification Search
CPC ......... G06T 7/0014; G06T 7/11; G06T 7/344; G06T 2207/20221; G06T 2207/30101;
(Continued)

(56) References Cited

U.S. PATENT DOCUMENTS

| 2005/0203373 A1 | 9/2005 | Boese | |
| 2010/0049038 A1* | 2/2010 | Florent | A61B 6/481 |
| | | | 600/425 |

(Continued)

FOREIGN PATENT DOCUMENTS

DE 102004004603 A1 8/2005

OTHER PUBLICATIONS

Jezzard et al., "Correction for Geometric Distortion in Echo Planar Images from B0 Field Variations", Jul. 1995, Williams and Wilkins, Magnetic Resonance in Medicine, vol. 34, p. 65-73 (Year: 1995).*

(Continued)

*Primary Examiner* — Vincent Rudolph
*Assistant Examiner* — Timothy Choi
(74) *Attorney, Agent, or Firm* — Lempia Summerfield Katz LLC

(57) ABSTRACT

A weighting for a roadmap method is automatically determined. A first or a second weighting image is generated from an anatomical image and an object image. For this purpose, a prespecified first weighting value is assigned to pixels belonging to a prespecified anatomical feature or to an instrument. Other pixels are assigned increasingly small weighting values at increasing distances from the anatomical feature or from the instrument toward an edge of a respective recording region according to a prespecified monotonously decreasing function in dependence upon the location. An overall weighting image is generated by combining the first and the second weighting images with one another and/or a (Continued)

region of interest determined using the overall weighting image are then provided as input data for an image processing algorithm.

15 Claims, 3 Drawing Sheets

(51) Int. Cl.
*G06T 7/33* (2017.01)
*G06T 7/11* (2017.01)
*A61B 34/20* (2016.01)
*A61B 34/10* (2016.01)

(52) U.S. Cl.
CPC . *A61B 2034/107* (2016.02); *A61B 2034/2065* (2016.02); *G06T 2207/10116* (2013.01); *G06T 2207/30021* (2013.01); *G06T 2207/30101* (2013.01)

(58) Field of Classification Search
CPC .............. G16H 30/40; A61B 2034/107; A61B 2034/2046; A61B 2034/2055; A61B 2034/2065; A61B 34/20
See application file for complete search history.

(56) References Cited

U.S. PATENT DOCUMENTS

| | | | |
|---|---|---|---|
| 2011/0235889 A1* | 9/2011 | Spahn | G06T 5/50 382/132 |
| 2011/0293164 A1* | 12/2011 | Sato | G06T 7/30 382/132 |
| 2013/0329030 A1* | 12/2013 | Tolkowsky | A61B 6/481 348/77 |
| 2015/0179148 A1* | 6/2015 | Auvray | A61B 6/5288 345/629 |
| 2017/0316602 A1* | 11/2017 | Smirnov | G06T 5/50 |
| 2018/0005372 A1* | 1/2018 | Wang | G06T 7/0012 |

OTHER PUBLICATIONS

Bar-Kochba et al., "A Fast Iterative Digital Volume Correlation Algorithm for Large Deformations", Aug. 2014, Society for Experimental Mechanics, Experimental Mechanics, vol. 55, p. 261-274. (Year: 2014).*

Rivaz et al., "Self-similarity weighted mutual information: A new nonrigid image registration metric", Dec. 2013, Elsevier, Medical Image Analysis, vol. 18, p. 343-358. (Year: 2013).*

German Office Action for German Application No. 10 2018 211 477.3 dated Jun. 14, 2019.

* cited by examiner

METHOD FOR AUTOMATICALLY DETERMINING A WEIGHTING FOR A ROADMAP METHOD, COMPUTER PROGRAM, DATA MEMORY AND CORRESPONDING IMAGING APPARATUS

RELATED CASE

This application claims the benefit of DE 10 2018 211 477.3, filed on Jul. 11, 2018, which is hereby incorporated by reference in its entirety.

FIELD

The present embodiments relate to a method for automatically determining a weighting for a roadmap method, a corresponding computer program, a data memory with such a computer program and a corresponding imaging apparatus for the roadmap method. The present embodiments are suitable for application in conjunction with medical imaging, but can in principle also be used in other sectors, for example industrial sectors.

BACKGROUND

Roadmap methods or a roadmap mode are methods that are known per se in medical imaging, in particular in interventional radiology. The roadmap methods are usually double subtraction methods in which two subtraction images are overlaid. In fluoroscopy, for example, first a vascular image, i.e. for a first subtraction image, an image of a vessel or vascular tree, can be generated in that a previously recorded mask image is subtracted from a contrast-agent image recorded after injection of a contrast agent. For the second of the subtraction images, a so-called device image can be generated in that a mask image recorded before the introduction of a respective medical object is subtracted from a live image recorded during a corresponding intervention. Therefore, in this case, the first subtraction image ideally only contains the vessels, while the device image ideally only depicts the respective medical object. Then, the overlaying of these images can be used as a navigation aid in the live imaging during the intervention, in order, for example to avoid multiple contrast agent injections and additional recordings that would entail a respective patient being exposed to ultimately unnecessary additional radiation and contrast agent.

However, in practice, the overlaying of the two subtraction images can be problematic since, for example, a movement of the patient and/or the imaging apparatus can complicate registration of the images and result in motion artifacts in the overlaying or a corresponding overlay image—also called a roadmap image. Motion artifacts of this kind and/or misregistrations can significantly complicate identifiability and image evaluation.

One solution used to date uses so-called pixel-shift or pixel-shifting algorithms, which attempt to register the two subtraction images with respect to one other using an image-based method and, for this purpose, to determine corresponding motion vectors according to which one of the two images has to be shifted for motion compensation in order to achieve accurate registration or overlaying. However, this method reaches its limits when, for example, relatively large regions are mapped, different movements have taken place in different sub-regions of the images, and/or relevant working areas and image areas—also called regions of interest (ROIs)—shift during the intervention.

Here, currently known methods and apparatuses cannot usually achieve a satisfactory performance, and/or the workflow is adversely affected since, for example, the respective staff have to adjust corresponding settings manually during the intervention.

SUMMARY AND DETAILED DESCRIPTION

The object of the present embodiments is to enable an improved roadmap method. Advantageous embodiments and developments are disclosed herein.

A method according to the one embodiment is used for automatically determining a weighting for images of a target object obtained by an imaging apparatus for a roadmap method. The target object can in particular be a patient or a sub-region of a patient, which is mapped by the imaging apparatus. However, the present method can also, for example, be applied to any objects that can be mapped with the respective imaging apparatus or imaging modality used in each case. The imaging apparatus can preferably be an X-ray apparatus, for example a C-arm apparatus. However, as long as a roadmap mode is available. it is also possible to use other imaging apparatuses or imaging modalities.

With the method according to one embodiment, first an anatomical image of the target object depicting or mapping a prespecified segmented anatomical feature of the target object is provided. The anatomical image can in particular be a subtraction image, for example the vascular image already cited in the introduction. In this case, then, for example, the respective vessel or the respective vascular tree is the anatomical feature. The anatomical feature can, for example, be specified in that the imaging apparatus is aligned and configured appropriately to map this anatomical feature. However, it is also possible for a user to make a specific selection or marking. In a further method step of the method, an object image is provided, which depicts a segmented instrument, apparatus, object or tool (device) in the region of the target object, i.e. in a corresponding recording region of the imaging apparatus, wherein the recording region of the object image or for the object image at least substantially corresponds to a recording region of the anatomical image, i.e. a recording region of the imaging apparatus used or set for the recording. Therefore, in this context, the recording region is the segment of the patient or target object mapped or depicted by the respective image. In other words, therefore, the recording regions or image segments of the object image and the anatomical image overlay or overlap one another completely or at least substantially completely. The object image, also called the instrument image, can in particular be the device image already cited in the introduction. Therefore, the object image can in particular also be a subtraction image. Individual images used to generate the anatomical image and the object image, i.e., for example, respective mask images, a contrast-agent image and an examination or live image of the target object, can, therefore, be recorded under the same or at least substantially the same recording conditions, in particular without any interim movement or shifting of the imaging apparatus in order to ensure that the same recording region, i.e. image segment is present, i.e. used or mapped in each case. Therefore, the recording region corresponds to a mapped spatial region or sub-region of the target object.

The provision of the anatomical image and the object image can include the generation thereof. This provision can also include the acquisition or recording of respective images used to generate the anatomical image and/or the object image, in particular X-ray images. Alternatively, provision can be that a corresponding data memory is provided and some or all of said images are retrieved from the data memory by the imaging apparatus or a facility configured and used to execute the present method.

The instrument depicted in the object image can, for example, be a wire, a catheter, a stent, a probe, an endoscope, an X-ray opaque adhesive, a screw, a hook and/or the like. Ultimately, for the purposes of the present embodiments, the instrument can be virtually any, in particular synthetic, object used to influence the target object, which can be mapped by the imaging apparatus or the imaging modality used in each case.

In a further method step, a first weighting image is generated from the anatomical image and a second weighting image is generated from the object image. To generate the first weighting image, a prespecified first weighting value—for example 1 or 100%—is assigned or allocated to pixels or image regions belonging to the anatomical feature. Pixels or image regions at an edge of the recording region that do not belong to the anatomical feature are assigned or allocated a prespecified second weighting value that is smaller than the first weighting value—for example 0 or 0%. Pixels or image regions between these pixels or image regions, i.e. between the anatomical feature and the edge of the recording region, are in each case assigned or allocated a weighting value between the first and the second weighting value according to a prespecified monotonously decreasing function in dependence on a location of the respective pixel or image region in the recording region or in the anatomical image. Similarly, to generate the second weighting image, pixels or image regions belonging to the instrument are assigned the prespecified first weighting value or another prespecified first weighting value and pixels or image regions at an edge of the recording region that do not belong to the instrument are assigned or allocated the, or a, prespecified second weighting value that is smaller than the first weighting value. Intermediate pixels, i.e. pixels between the instrument and the edge of the recording region, are in each case assigned or allocated a weighting value between the first and the second weighting value according to the, or a, prespecified monotonously decreasing function in dependence on the location of the respective pixel or image region in the recording region or in the object image.

Therefore, the closer a pixel or image region between the edge and the anatomical feature or between the edge and the instrument is to the anatomical feature or the instrument, the higher or greater its weighting value may be and correspondingly, the closer it is to the edge, the smaller or lower its weighting value may be. The weighting values assigned to the pixels or image regions between the edge and the anatomical feature or the instrument can include the prespecified second weighting value, but should preferably be different from the prespecified first weighting value. This enables it to be ensured that a pixel or image region belonging to or allocated to the anatomical feature or the instrument or to a to the anatomical feature or the instrument always has the greatest weight, i.e. is or will be weighted more heavily.

The first weighting value and the second weighting value and the prespecified function can be identical for the first and second weighting images in order to improve consistency and transparency and minimize the outlay for the method. However, it is also in principle possible to use different first weighting values, second weighting values and/or functions for the first and second weighting images. This can, for example, be advantageous when the anatomical image and the object image have significantly different image qualities or image properties, for example a different level of noise, different contrast ratios, a different definition and/or the like. In such cases, individually adapted weighting values and/or an individually adapted prespecified function for the weighting or a profile of the weighting values can ultimately enable improved image quality to be achieved for a resultant overlaying or roadmap image generated from the object image and the anatomical image.

Therefore, the first and the second weighting image can have the same dimensions as the anatomical image or the object image, wherein each pixel of the weighting images is allocated to a corresponding pixel of the anatomical image or the object image and hence allocates a respective weighting value thereto.

In a further method step, an overall weighting image is generated by combining the first weighting image and the second weighting image with one another. This combination can be achieved by overlaying, in particular by adding, the two weighting images. Therefore, the overall weighting image indicates the combination or total of the weightings or weighting profiles from the two weighting images. Preferably, the overall weighting image or the weighting values thereof can be normalized to 1 so that, therefore, the pixels or image regions most heavily weighted in the, or by the, overall weighting image have a weighting value of 1. This can advantageously simplify further processing and the transparency or interpretation of the results obtained and possibly contribute to a reduced error rate. Therefore, in the weighting images, the pixels or image regions belonging to the anatomical feature and the instrument can have the weighting value 1, the pixels at the edge of the recording region or the pixels or image regions at the edge of the respective weighting image that do not belong to the anatomical feature or the instrument can have the weighting value 0 and the intermediate pixels or image regions can have weighting values between 0 and 1 in dependence on their location.

In a further method step, the overall weighting image and/or a region of interest of the anatomical and/or object image or the recording region determined using the overall weighting image is provided, i.e., for example, transmitted, as input data for, or to, an image processing algorithm. The image processing algorithm can further process the anatomical image and/or the object image in dependence on this input data, for example overlay them on one another in order to generate the roadmap image. The image processing algorithm can also, for example, perform segmentation, feature detection and/or the like, wherein advantageously using or taking account of the overall weighting image, i.e. the weighting disclosed therein for each pixel or image region, results in a corresponding prioritization. This, for example, enables more computing time or computing effort to be used for pixels or image regions with a higher weighting value. If, for example, the image processing algorithm is not able to achieve or ensure the same accuracy or precision for a respective operation over a respective entire recording region, i.e. over a respective overall image area, it is therefore possible to prioritize pixels or image regions with a higher weighting value, in particular the pixels or image regions with a weighting value of 1. Therefore, the overall weighting image can specify or represent the condition that the best achievable result is always achieved for pixels or image regions with the weighting value 1 or a weighting value above a prespecified threshold value, possibly at the expense of quality, accuracy or precision in pixels or image regions with a lower weighting value.

The method according to one embodiment is based on the assumption that, for a respective user or with a respective application, the most important or most relevant image regions are those belonging to the prespecified anatomical feature and those belonging to the instrument. Since precisely these image regions are automatically weighted most heavily by the overall weighting image, these image regions can then be prioritized by the image processing algorithm. As a result, therefore, the best achievable accuracy or image quality is obtained in these image regions, in particular when this cannot be achieved uniformly over the entire recording region. As described, this can, for example, be the case if different movements of the target object have occurred in different sub-regions of the recording region, as can, for example, be the case due to the flexibility of mapped biological tissue.

The fact that the overall weighting image is generated automatically also enables the region of interest to be determined automatically, in the simplest case by a threshold method, for example. Hence, the method according to one embodiment can advantageously improve workflow with the roadmap method since, for example, the respective region of interest no longer has to be manually adapted or tracked by the staff or the user during the intervention. In addition, the overall weighting image advantageously always enables an optimum result, i.e., for example, optimum image quality or accuracy, to be achieved in the most relevant region, i.e. in the image regions with the highest weighting value, in particular also in cases when there is insufficient computing power and/or time available to process the entire recording region with the same accuracy, i.e. with the same computing effort. Thus, it is possible, for example by particularly simple setting or specification of a threshold value for the weighting value in dependence on the available computing power and/or time, to set, for example, the degree to which less relevant image regions, i.e. those with a weighting value below the threshold value, will be taken into account or processed by the image processing algorithm.

Although this is not described in detail here, the anatomical image and the object image can be generated automatically in manner that is known per se, for example by the application of automatic segmentation algorithms for the automatic segmentation of the anatomical feature or the instrument.

Therefore, the present method can be applied or used in a completely automated manner as a preliminary stage for further processing of the image obtained by means of the imaging apparatus.

In one advantageous embodiment, the region of interest in the anatomical image and in the object image is determined as the respective image regions thereof corresponding to the pixels or image regions of the overall weighting image with a weighting value greater than a prespecified weight threshold value. Since the image regions belonging to the anatomical feature and the instrument automatically always have the highest weighting values, it is automatically ensured that the anatomical feature and the instrument are located within the region of interest (ROI). Hence, it is advantageously no longer necessary to specify or track the region of interest manually. This can simplify, i.e. improve, the workflow. It is also possible to avoid manual specification by the user of the region of interest or an image region to be treated as a region of interest and hence exclude this as an error source. This is particularly advantageous since it has been found that such a method of specification is frequently error-prone. In contrast, with the present method, the weight threshold value can be specified once before or at the start of the intervention and then no longer needs to be changed or adapted during the intervention, wherein, however, the region of interest can nevertheless be updated or tracked automatically during the intervention. Since the region of interest automatically determined in accordance with the present method always automatically includes the instrument used in each case, the region of interest determined in accordance with the present method is also called an interventional region of interest (IROI).

It is emphasized at this point that the present invention does not encompass or claim the intervention as such or a corresponding surgical procedure. Rather, mention of the intervention is merely an expression of the fact that the method according to the invention can be advantageously applied during such an intervention. Therefore, the method according to the invention can also be understood as a method for operating the imaging apparatus or a corresponding data processing facility for processing the images named or corresponding image data.

In a further advantageous embodiment, the image processing algorithm is a pixel-shift algorithm, which registers the object image to the anatomical image for overlaying and, for this purpose, wholly or partially compensates a movement of the target object and/or the imaging apparatus between respective acquisition time points of the anatomical image and the object image or respective images used for the generation thereof taking account of the overall weighting image. Herein, image regions that are allocated a higher weighting value, i.e. a higher weight, by the overall weighting image are then prioritized over other image regions with a lower weighting value. Therefore, if the movement is not compensated simultaneously in all image regions, the movement is preferably compensated for image regions with the highest weighting value or a relatively higher weighting value in each case. In this context, herein a movement is in particular a relative movement between the target object and the imaging apparatus, wherein the target object can move as a whole or only in one or more sub-regions.

Therefore, the pixel-shift algorithm generates a roadmap image, in which the object image and the anatomical image are overlaid or mixed, from the object image and the anatomical image so that the roadmap image therefore represents both the anatomical feature and the instrument positioned correctly relative thereto, i.e. corresponding as closely as possible to reality.

If no movement has taken place or if the target object has moved uniformly as a whole relative to the imaging apparatus, the roadmap image generated by the present method corresponds to a result that can also be achieved with conventional methods. However, in practice different movements or components of movements are often present that are not global, i.e. do not occur in the entire recording region, but only locally, i.e. only in a sub-region of the recording region. In such cases, it is not usually possible for the registration to be performed over the entire recording region with the same accuracy. Conventional methods can then result in suboptimal average registration or overlay accuracy being achieved or set over the entire recording region or, for example, the best registration or overlay accuracy being achieved or set in a region that is not relevant for the respective intervention. On the other hand, with the present method, the overall weighting image provides the pixel-shift algorithm with a measure for taking account of pixels or image regions for the registration.

Therefore, overall, the present method enables an automatic calculation of the overall weighting image and the interventional region of interest and hence offers a pragmatic and clinically relevant solution for the problem of compensation or registration of complex and local movements, in which the most favorable, i.e. best or most accurate, registration and overlaying is performed specifically in the interventional region of interest, i.e. for the image regions with the highest weighting value. Hence, optimal image quality is achieved in these image regions; this is particularly advantageous since here the respective user benefits most from optimal registration or overlay accuracy. In order to achieve this, according to the overall weighting image, it may be necessary for correspondingly larger misregistrations or inaccuracies in image regions with lower weighting values to be taken into account. However, overall this still represents an optimization or improvement since it exploits precisely the circumstance that these image regions are not relevant or are less relevant for the respective user or the respective application. Hence, account is automatically taken of the fact that features present outside the anatomical feature or outside the instrument or details in the anatomical image or in the object image could possibly be image artifacts, for example have occurred due to inaccurate or faulty segmentation or due to movements of the target object between respective recording time points of the individual images used to generate the anatomical image or the object image.

In a further advantageous embodiment, to generate the first and the second weighting images from the anatomical image or from the object image, first a respective binary image is generated. For this purpose, a first binary value, for example 1, is assigned or allocated to the pixels or image regions belonging to the anatomical feature or the instrument and a second binary value, for example 0, is assigned or allocated to the respective remaining pixels or image regions. Then the first weighting value is correspondingly assigned to the pixels or image regions with the first binary value. Since, therefore, these binary images are, or can be, much less complex than the anatomical image and the object image, this can reduce the outlay for the subsequent processing steps. For the generation of the binary images, it is, for example, possible for a segmentation threshold value to be prespecified. Therefore, pixels or image regions, with pixel values, i.e. brightness or intensity values, for example on the Hounsfield scale, above the segmentation threshold value are understood, or treated or interpreted as belonging to the anatomical feature or the instrument or allocated to the instrument or the anatomical feature or the instrument. This advantageously offers a further possibility for refining the segmentation, i.e. for adapting or setting the image regions belonging to the anatomical feature or the instrument as needed or required or, for example, according to the image quality in a particularly simple manner.

In a further advantageous embodiment, a respective safety region is defined, which adjoins and surrounds the pixels or image regions belonging to the anatomical feature or the instrument. These safety regions are then in each case assigned the same weighting value, in particular therefore the first weighting value, as the pixels or image regions belonging to the anatomical feature or the instrument. In other words, therefore, the image region belonging in each case to the anatomical feature or the instrument can be dilatated or expanded or enlarged. The pixels in the safety regions are then treated or interpreted as belonging to the anatomical feature or the instrument, i.e. for example allocated to the anatomical feature or the instrument.

Preferably, the respective safety region, in each case, is locally at least half the size of a closest or largest diameter of the anatomical feature or the instrument. These safety regions can advantageously enable account to be taken of shifts and changes to the shape and/or size of the anatomical feature. Hence, it is also possible to ensure that, even when changes of this kind occur during the intervention, the anatomical feature and the instrument remain within the region of interest, i.e. the image regions in which the shifted or changed anatomical feature or instrument is then located, reliably continue to have the greatest weighting values, in particular the first weighting value.

In a specific example, the anatomical feature can, for example, be a vessel, which is shifted, stretched or expanded by the introduction of a wire or catheter serving as the instrument. If not immediately followed by the recording of a new image from which the new situation can be identified and/or a recalculation of the region of interest, without the safety regions, the anatomical feature and/or the instrument could shift into a region with a lower weighting value. This can advantageously be avoided by the safety regions. It is also possible for further image processing or image editing steps, for example further morphological operations to be carried out, i.e. applied to the anatomical image, the object image and/or the binary images and/or weighting images generated therefrom. Preferably, for example, an erosion operation can be carried out in order to remove isolated individual pixels or isolated image regions from a prespecified maximum number of adjacent pixels surrounded in each case by pixels or image regions with a different value, i.e. to set them to the value of the surrounding pixels or image regions in each case. This advantageously enables the respective image to be smoothed and accordingly simplified and particularly consistent further processing to be achieved.

In a further advantageous embodiment, a nonlinear function, in particular an exponential function or a polynomial function is used as the prespecified monotonously decreasing function. The use or application of such a function therefore causes the weighting values to fall nonlinearly from the image regions belonging to the anatomical feature or the instrument toward the edge of the recording region. It has been found that overall this enables the achievement of improved or optimized identifiability of the resulting roadmap image. Particularly advantageously, it is possible to use a continuous nonlinear function since, in contrast to a step or jump function, this enables the attenuation or obliteration of registration errors for the observer and this can ultimately simplify the interpretation or evaluation of the depicted image content.

In a further advantageous embodiment, a sequence of a plurality of object images is generated and provided and the first weighting image is generated, in each case updated, not for all images of this plurality of object images, but only for images selected in accordance with a prespecified selection rule. In particular, it can be provided that a, or the, first weighting image is only generated for each n-th image of the plurality of object images, wherein n indicates a prespecified number. Therefore, if n=3 is specified, a, or the, respective first weighting image is only generated in the manner described for each third object image. This advantageously enables savings to be made on calculation costs or calculation resources thus enabling the method also to be executed on less powerful hardware, for example. This embodiment is based on the knowledge that the object usually moves relatively slowly so that a misregistration or a corresponding overlay error resulting from a change between two immediately successive object images is negligible for practical applications even without the regeneration of an updated weighting image.

However, it can preferably be provided that when this embodiment of the method is used in the manner described, a safety region is provided around the instrument and/or the region of interest determined using the overall weighting image is automatically enlarged by a prespecified factor. For further simplification, here it can also be provided that the region of interest is determined as a, or with a, simple geometric shape, for example as a circle or as a rectangle, which completely encloses the image region, wherein pixels inside this circle or in this rectangle can then be assigned or allocated the maximum or the first weighting value or a weighting value above a prespecified threshold value. Such a case is, therefore, simplified in that the region of interest does not need to be determined in such a way that its shape or contour follows a shape or contour of the image regions belonging to the anatomical feature and the instrument.

In a further advantageous embodiment, a plurality of object images is generated. A respective difference image is then generated in that an image, in each case previously generated, of the plurality of object images is subtracted from at least one image of the plurality of object images. In the simplest case, therefore, only two object images are generated, for example before and after a movement of the instrument. Accordingly, then also only one single difference image is generated in that the first-generated object image is subtracted from the last-generated object image. However, this procedure can also be extended to ultimately any number of object images. It is then possible for a difference image to be generated for each of the object images in that a previously recorded object image, in particular the object image recorded immediately beforehand, is subtracted. However, it can also be provided that, for example, a respective difference image is only generated for each n-th object image. This can, for example, be sufficient when the instrument does not move, or only moves insignificantly between the respective recording time points of two successive object images. Therefore, the difference image or the difference images ideally only show the instrument or a sub-region of the instrument in the image region in which the instrument is located in the later-recorded object image in each case, but not in the earlier-recorded object image in each case, which is subtracted.

Hence, the difference image represents a movement of the instrument between the recording time points of the two object images used. A respective difference weighting image is then generated from the difference image or from the difference images in that a first difference weighting value is allocated to pixels or image regions of the difference image or a first binary image generated therefrom belonging to the instrument and a second difference weighting value is assigned to the remaining image regions of the difference image or of the binary image. Herein, the second difference weighting value is smaller than the first difference weighting value. The difference weighting values can correspond to the first and second weighting values or be specified in some other way.

To generate the overall weighting image, the first and the second weighting image and the difference weighting image are then combined with one another. This procedure results in dynamic updating of the region with the highest weighting value such that the image region in which the instrument last moved always has the greatest weighting value. This can, for example, then occur and be particularly advantageous if different vascular regions are treated or manipulated by the instrument during the intervention. Hence, the described method enables the region of interest to be further refined, i.e. adapted more accurately to the respective situation or the respective requirement. Hence, it can be achieved or ensured that, for example in the resulting roadmap image, optimal registration, i.e. overlay accuracy, is always achieved in the image region in which in each case the target object is currently being manipulated by means of the instrument. This can provide optimum support for the user.

In this case once again the combination of weighting images and the difference weighting image can preferably provide that these or the pixel values, image values or weighting values thereof are added to within pixel accuracy. Preferably, the resulting overall weighting image can be normalized, for example to 1. It is also possible to use the prespecified monotonously decreasing function or another prespecified function to generate the respective difference weighting image. It can, for example, be possible to use a continuous exponential function or polynomial function to generate the first and the second weighting image and a step or jump function to generate the difference weighting image. As a result, the region in which the instrument is currently located or in which the instrument last moved can, on the one hand, be particularly emphasized, while, on the other, the continuous course of the function used for the first and second weighting image simultaneously enables a deflecting discontinuity, for example an abrupt shift or shear, in the roadmap image to be avoided.

A further aspect is a computer program or computer program product, which codes or represents the method steps of at least one embodiment of the method and which is configured to be loaded into a non-transitory data memory, in particular an electronic and/or electronically readable data memory of a control apparatus of an imaging apparatus in order to execute the method steps. Therefore, the computer program can include a program or instructions for carrying out the method when the computer program is executed by the control apparatus (e.g., image processor).

A further aspect is a non-transitory data memory, in particular an electronic and/or electronically readable data memory, or data carrier for a control apparatus of an imaging apparatus. The data memory is used to store a program code including at least one embodiment of the computer program. The data memory can also be used to store code, in particular as part of the program code, further control instructions for the control apparatus and/or the imaging apparatus. The program code stored on the data memory is therefore in particular embodied and configured, when the data memory is used in the control apparatus of the imaging apparatus and when the program code is executed by the control apparatus, in particular by a microprocessor and/or microcontroller of the control apparatus, to execute or effect at least one embodiment of the method.

A further aspect is an imaging apparatus for roadmap imaging. The imaging apparatus includes an acquisition facility for acquiring images of a target object, in particular a patient, with a control apparatus and a data memory according to one or more embodiments. Herein, the control apparatus is configured to process the acquired images. In particular, the control apparatus can be configured to execute the program code stored on the data memory and for this purpose include a corresponding processor facility connected to the data memory. The control apparatus of the imaging apparatus can, therefore, in particular be the control apparatus cited in connection with the data memory according to one of the embodiments and/or in connection with the computer program according to one of the embodiments. Accordingly, the imaging apparatus can in particular be the imaging apparatus cited in connection with the data memory according to one of the embodiments, the computer program according to one of the embodiments, and/or the method according to one of the embodiments. Accordingly, therefore, the imaging apparatus can include some or all of the properties and/or components cited in connection with the remaining aspects. Therefore, the imaging apparatus can preferably, for example, be a C-arm X-ray apparatus. Moreover, the imaging apparatus can include further components or units, such as, for example, a display facility for displaying the described roadmap image generated from the anatomical image and the object image or the like.

The properties and developments of the method disclosed above and below and the corresponding advantages can in each case be transferred analogously to the other aspects, i.e. to the computer program, the data memory, and/or the imaging apparatus, and vice versa. Therefore, this invention also includes developments of the method according to the invention, the imaging apparatus according to the invention, the computer program according to the invention and data memory according to the invention with embodiments that, in order to avoid unnecessary redundancy, are not explicitly described here in the respective combination or described separately for each aspect of the invention.

BRIEF DESCRIPTION OF THE DRAWINGS

Further features, details and advantages may be derived from the following description of preferred exemplary embodiments and with reference to the drawings, which show.

DETAILED DESCRIPTION

Figure 1:
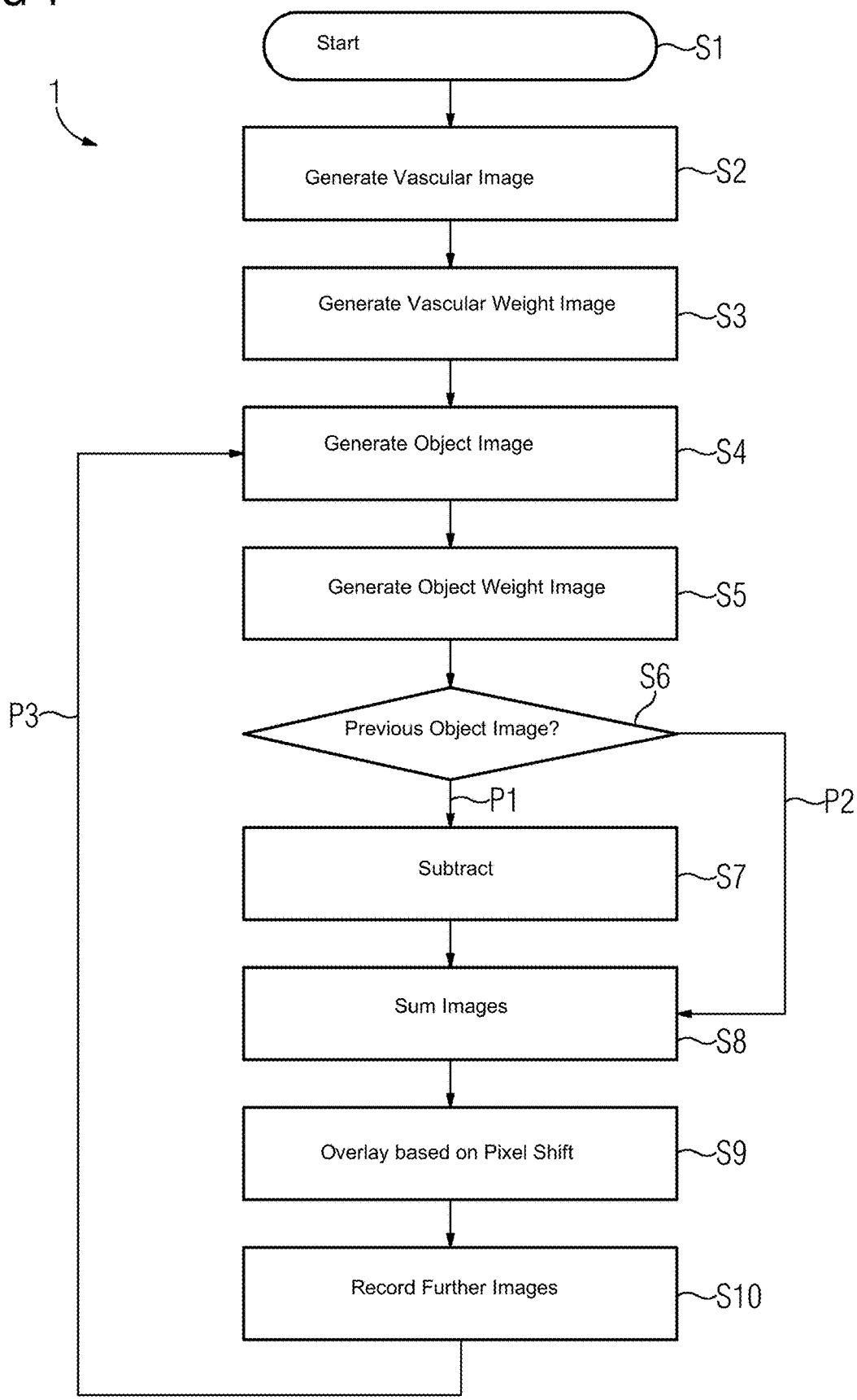
FIG. 1 is an exemplary schematic flow diagram of a method for automatically determining a weighting for images of a target object obtained by means of an imaging apparatus.

The exemplary embodiments explained in the following are preferred embodiments of the invention. In the exemplary embodiments, the described components of the embodiments in each case represent individual features of the invention to be considered independently of one another, which in each case also develop the invention independently of one another and thus are also to be considered as part of the invention individually or in a different combination than the one shown. Furthermore, the described embodiments can also be complemented by further, already described, features of the invention.

In the figures, elements which are the same or functionally equivalent or which correspond to one another are in each case provided with the same reference characters.

FIG. 1 shows an exemplary schematic flow diagram 1 of a method for automatically determining a pixel-precise weighting for images of a target object obtained by an imaging apparatus. This method can, for example, be present or implemented in the form of a computer program or computer program product and then be stored on an electronically readable data carrier, which is not shown in detail here, possibly with further electronically readable control information stored thereupon. To execute or perform the method, the computer program can then be executed automatically by a control apparatus of the imaging apparatus.

The method is explained below with references to FIG. 2 to FIG. 6. Herein, the method is described—without being restricted thereto—for a fluoroscopy X-ray apparatus.

In a method step S1, the method is started. Here it is, for example, possible for a target object, in the present case, therefore, a patient to be mapped. The patient is positioned on a patient table of the imaging apparatus. In addition, here a respective user can issue or input specifications which are then taken into account or used during the course of the method. Thus, it is, for example, possible for a sub-region of the patient to be mapped to be specified or defined.

Figure 2:
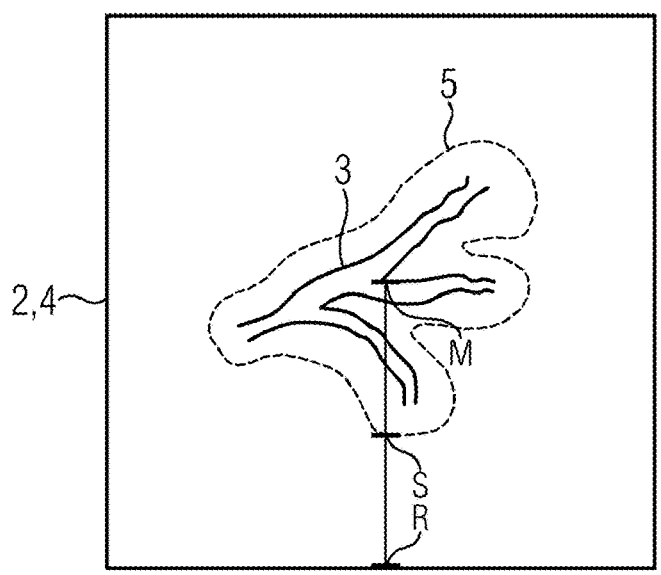
FIG. 2 is an example schematic vascular image.

In the present case, a vessel 3 of the patient depicted in a vascular image 2 in FIG. 2 is mapped as the target object. For this purpose, in a method step S2, first a mask image is recorded of the prespecified sub-region of the patient, corresponding to a recording region 4 mapped by or in the vascular image 2. Then, a contrast agent is introduced into the vessel 3 and then a contrast-agent image of the vessel 3 or of the recording region 4 is recorded. The mask image is then subtracted from the contrast-agent image and as a result the vascular image 2 generated in that it then only contains, i.e. depicts, the vessel 3.

In a method step S3, a first weighting image is generated from the vascular image 2. For this, the vascular image 2 as such is considered in context and an intensity analysis of the vascular image 2 performed in order to identify or detect the vessel 3. For this intensity analysis, in the present case, an automatic threshold-value-based segmentation is performed in order to identify the pixels or image regions of the vascular image 2 that belong to the vessel 3, i.e. map or depict the vessel 3. Then, a corresponding image processing facility, for example the control apparatus of the imaging apparatus, applies several morphological operations to the segmented vascular image 2. In the present case, these morphological operations include dilatation and erosion. Erosion smooths the vascular image 2 and delimits the coherent image region belonging to the vessel 3.

The dilatation uses uniform enlargement of this coherent region by at least 50% of a greatest diameter of the vessel 3 to define a safety region 5 around the actual vessel 3 or the actual image region depicting the vessel 3. This dilatation, i.e. enlargement or expansion, of the image region belonging to the vessel 3 enables changes that occur during an intervention, for example an elongation of the vessel 3 due to the introduction of an instrument 7 (see FIG. 3), to be taken into account or picked up. For simplification, now a first binary image is generated based on the segmented vascular image 2 taking account of the safety region 5 in that all the pixels in the safety region 5, including the pixels mapping the vessel 3, are assigned a first binary value of 1 and all the remaining pixels, i.e. pixels outside the safety region 5, of the vascular image 2 or the recording region 4 are assigned a second binary value of 0. Therefore, in the binary image, a value of 1 for a specific pixel indicates that this pixel belongs to the vessel 3 including the safety region 5.

Then, to calculate or generate the first weighting image, a region of the binary image that has the value 1, i.e. belongs to the vessel 3 including the safety region 5, is given a first weighting value of 1. Then, starting from the safety region 5 toward an outer edge region of the recording region 4, the intermediate regions or pixels of the binary image are assigned a respective weighting value according to a prespecified nonlinear, in particular exponential or polynomial, function in dependence on a respective location within the recording region 4. Herein, the prespecified nonlinear function is selected such that pixels at the edge of the recording region 4 are assigned a second prespecified weighting value of 0. Therefore, as the distance from the safety region 5 to the edge of the recording region 4 increases, the weighting value is continued or extrapolated in accordance with the prespecified nonlinear function up to the weighting value 0 at the edge of the recording region 4. As a result, image regions or anatomical regions outside the safety region 5 are given a less strong weighting than the safety region 5 including the vessel 3. Therefore, the first weighting image generated in this way assigns a weighting value for the further method to each pixel of the binary image and hence also to each corresponding pixel of the vascular image 2.

Figure 3:
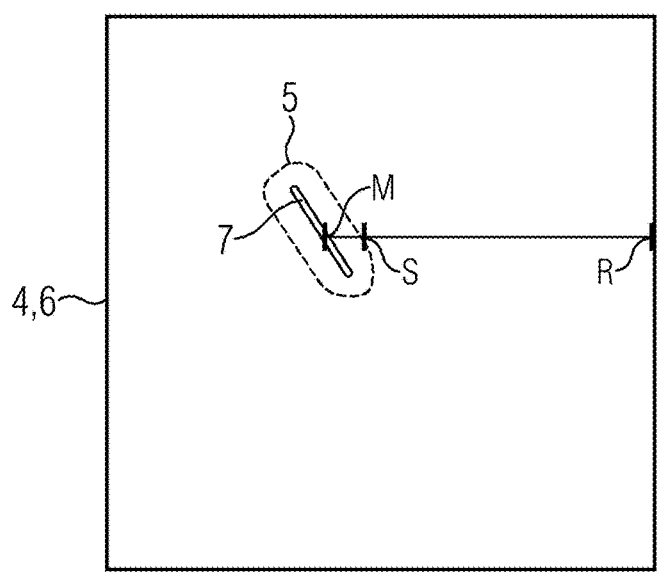
FIG. 3 is an example schematic object image.

In a method step S4, a schematically depicted object image according to FIG. 3 is generated. For this purpose, once again a mask image is recorded. When an instrument 7 has been introduced into the recording region 4, an examination or live image of the recording region 4 is recorded, in the present case by X-ray fluoroscopy. The mask image is subtracted from this live image in order to generate the object image 6 which then only contains, i.e. depicts, the instrument. The object image 6, usually also called the device image, is therefore typically produced by subtraction of the live image with a previously recorded anatomical mask. Ideally, herein, this only produces an image of the introduced instrument 7. In practice, however, the resulting object image 6 is usually not this clear but has further unwanted elements or artifacts. These are, for example, subtraction artifacts, which can be caused by a relative movement between the target object, i.e. here the vessel 3, and the imaging apparatus between respective recording time points of the live image and the anatomical mask image, by a change in the shape of an anatomy, i.e. the vessel 3, due to changed recording or mapping conditions, i.e., for example X-ray parameters, noise and/or the like. These artifacts complicate segmentation of the instrument 7. Nevertheless, a threshold-value-based automatic segmentation method that is known per se enables the instrument 7, like the vessel 3 previously, to be at least roughly segmented in order, therefore, to determine pixels or image regions in the object image 6 belonging to the instrument 3. Herein, a strongest signal, i.e. depending upon the embodiment, for example, a maximum or minimum intensity value, can be interpreted as representing the instrument 7.

Advantageously, a segmentation method based on machine learning can be used for the segmentation of the object image 6 or the instrument 7 and/or for the segmentation of the vascular image 2 of the vessel 3. It has been found that such methods are much less sensitive or less error-prone than usual threshold-value methods, which, in the case of a non-optimally selected threshold value can generate a faulty segmentation.

As in the case of the vascular image 2, corresponding morphological operations are also applied to the object image 6, i.e. here at least the erosion operation and dilatation, in order to determine and delimit the coherent image region belonging to the instrument 7, to smooth the object image 6 and to define a corresponding safety region 5 surrounding the instrument 7 in the object image 6. Then, as described in connection with the vascular image 2, a resulting intermediate result image is converted into a second binary image, wherein pixels or image regions which belong the instrument 7 or are within the safety region 5 are assigned the first binary value of 1 and the pixels outside the safety region 5 in the recording region 4 are assigned the second binary value of 0. Then, in a method step S5, here once again, the pixels or image regions with the binary value 1 are assigned the first weighting value of 1 and the remaining pixels with the binary value 0 are assigned gradually smaller weighting values according to their location within the recording region and their distance from the safety region 5 in accordance with the prespecified nonlinear function until finally, the second weighting value of 0 at the edge of the recording region 4 is achieved. Herein, it is in principle also possible for other weighting values to be specified or used, wherein, however, it is necessary to ensure that the safety region 5, including the vessel 3 or the instrument 7, is more heavily weighted than the remaining pixels or sub-regions or image regions of the recording region 4.

Figure 4:
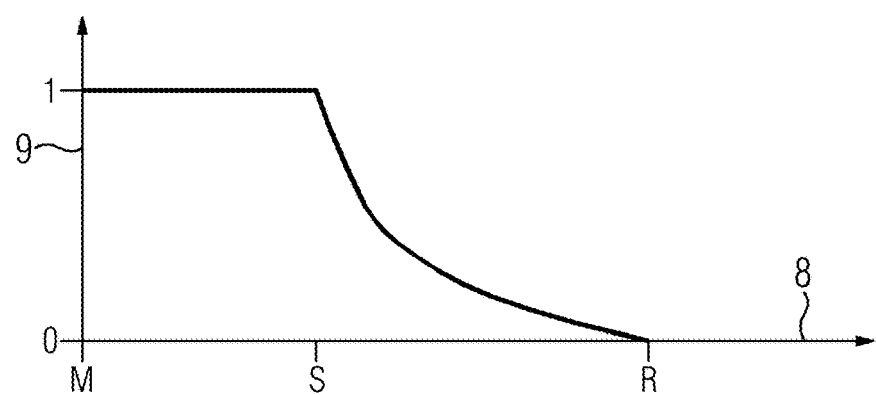
FIG. 4 is a diagram with an example weighting profile.

The diagram in FIG. 4 is an exemplary and schematic illustration of the profile of the weighting values in a segment of the weighting images, i.e. for a sub-region of the vascular image 2 and the object image 6. Here, a position is plotted on an x-axis 8 starting from a center point of the vessel 3 or the instrument 7 over a transition point S between the safety region 5 and the surrounding image regions up to an edge R of the recording region 4. The weighting value is plotted on a y-axis 9. It can be identified here that the pixels within the safety region 5, i.e. allocated to the vessel 3 or the instrument 7, are allocated the first weighting value 1 and, from the transition point S to the edge R of the recording region 4, the weighting value of the pixels arranged there decreases nonlinearly to the second weighting value 0 at the edge R. The profile depicted here should be understood as being purely exemplary and schematic since it is also possible for other functions to be selected, which, however, in principle have the same structure. The distance, size and scaling ratios should be understood as being schematic only since, for example, the distances between M, S and R in the vascular image 2 can differ from the corresponding distances in the object image 6.

In a method step S6, entails a query as to whether a previously generated object image, i.e. a previous or older iteration of the object image 6 has already been generated, i.e. is available. If this the case, the method follows a path P1 to a method step S7. In this method step S7, the previous object image available is then subtracted from the in each case current object image 6 in order to generate a difference image. Similarly to the already described weighting images, a difference weighting image is generated therefrom so that it is therefore possible to take account dynamically of a movement of the instrument 7 between the recording time points or generation time points of the object images 6.

If no such older object image is available, the method follows a path P2 directly to a method step S8.

Figure 5:
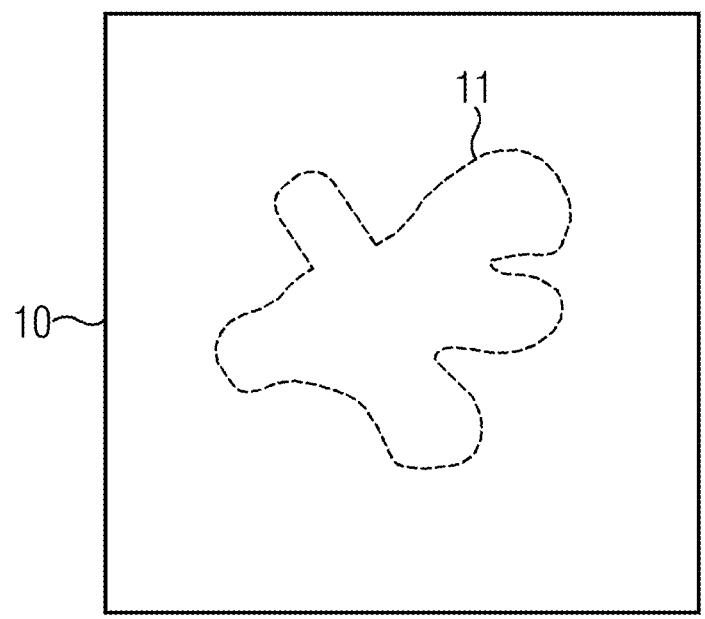
FIG. 5 is a schematic overall weighting image in one example.

In the method step S8, the weighting images generated from the vascular image 2 and the object image 6 and possibly the difference weighting image are added to one another and a resulting summation image normalized to 1 in order to generate an overall weighting image 10 as depicted in an exemplary and schematic manner in FIG. 5. Then, the overall weighting image 10 can then be used, for example by means of a threshold-value method, to determine an interventional region of interest 11. In the present case, this interventional region of interest 11 includes all the pixels allocated to the vessel 3, the instrument 7 and the respective safety regions 5 and thus indicates which image regions are particularly important for the respective current application. For purposes of simplification, it is also possible for the overall weighting image 10 to be converted into a binary image. Otherwise, the overall weighting image 10 has a similar weighting-value profile, as illustrated in FIG. 4. The sum weight disclosed in the overall weighting image 10 for each pixel, i.e. the respective overall weighting value of the respective pixel taking account of the vascular image 2 and the object image 6, advantageously enables less account to be taken subsequently of pixels or image regions with a relatively lower weight, i.e. with relatively lower relevance for the current application.

Figure 6:
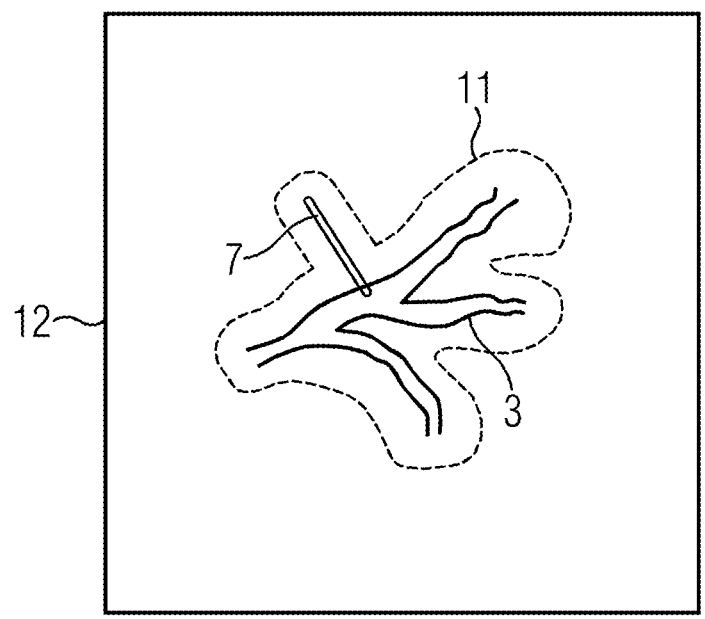
FIG. 6 is a schematic roadmap image obtained by overlaying the images from FIG. 2 and FIG. 3.

The overall weighting image 10 and the interventional region of interest 11 are then transferred to a pixel-shift algorithm. In a method step S9, this pixel-shift algorithm overlays the vascular image 2 and the object image 6 taking account of the overall weighting image 10 or the interventional region of interest 11 to generate a roadmap image 12 as depicted in FIG. 6 in an exemplary and schematic manner. For this, for motion compensation, the pixel-shift algorithm shifts individual sub-regions of the vascular image 2 and/or the object image 6 so that, at least in the interventional region of interest 11, i.e. in the image region containing the vessel 3 and the instrument 7, the registration and overlaying achieved is as accurate as possible since the overall weighting image 10 allocates the greatest weighting value, i.e. the greatest weight or the greatest relevance, to this image region. Therefore, the method is based on the assumption or finding that respective users or the like are able to view and identify the image region in which they are working with the instrument 7 in the best and most accurate manner and that a misregistration, i.e. a local relative movement during the overlaying of the vascular image 2 and the object image 6, causes the greatest disruption there and therefore requires prioritized correction, while less account needs to be taken of image regions outside the interventional region of interest 11 and the local registration or overlay accuracy there in accordance with the overall weighting image 10. Therefore, the registration of the object image 6 with the vascular image 2 is specifically prioritized for the interventional region of interest 11.

In the further course of the method, in a method step S10, further live images of the recording region 4 can be recorded. It is then possible for a respective new object image 6 to be created for each of these newly recorded live images. It is then possible for the method steps S4 or S5 to S9 to be repeated for each of these in each case newly created object images 6 in order to generate an in each case updated roadmap image 12. Therefore, it is also possible for the second weighting image and hence also the overall weighting image 10 to be automatically and dynamically updated during the live imaging in order always to obtain the best possible image quality of the respective roadmap image 12 in the respective interventional region of interest 11 during the entire intervention or application. Alternatively, and to save calculation resources, this dynamic updating can also, for example, be performed for only a certain number of live or object images 6, for example for each n-th image.

Therefore, the method described enables the respective interventional region of interest 11 to be individually localized automatically for each individual application and the performance of the pixel-shift algorithm used to generate the respective roadmap image 12 to be improved. The method offers an automatic calculation of an IROI-based weighting mask, i.e. the overall weighting image 10, in order to enable targeted pixel shifting for motion compensation in a 2D-roadmap method.

Although the invention has been illustrated and described in greater detail with the preferred exemplary embodiment, the invention is not restricted to the examples disclosed, and other variants can be derived therefrom by a person skilled in the art, without going beyond the scope of the invention. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

The invention claimed is:

1. A method for automatically determining a weighting for images of a target object obtained by an imaging apparatus for roadmap imaging, the method comprising:
   providing an anatomical image depicting a prespecified segmented anatomical feature of the target object,
   providing an object image depicting a segmented instrument in a region of the target object, wherein a recording region of the object image corresponds to a recording region of the anatomical image,
   generating a first weighting image from the anatomical image and a second weighting image from the object image in that a prespecified first weighting value is assigned in each case to pixels belonging to the anatomical feature or to pixels belonging to the instrument, in each case pixels at an edge of the recording region that do not belong to the anatomical feature or do not belong to the instrument are assigned a prespecified second weighting value that is smaller than the first weighting value, and intermediate pixels are assigned a weighting value between the first and the second weighting values according to a prespecified monotonously decreasing function in dependence on a location of the respective pixel in the recording region,
   generating an overall weighting image from combination of the first and the second weighting images with one another, and
   providing the overall weighting image and/or a region of interest determined using the overall weighting image as input data for an image processing algorithm,
   wherein the image processing algorithm is a pixel-shift algorithm, which registers the object image to the anatomical image for overlaying and, for this purpose, compensates a movement of the target object and/or the imaging apparatus between respective acquisition time points of the anatomical image and the object image taking account of the overall weighting image, and
   wherein image regions that are allocated a relatively higher weighting value by the overall weighting image are prioritized for a greater registration accuracy in motion compensation by the pixel-shift algorithm over other image regions allocated a relatively lower weighting value and a relatively lesser registration accuracy.

2. The method as claimed in claimed 1, characterized in that the region of interest in the anatomical image and in the object image is determined as the respective image regions thereof corresponding to the pixels of the overall weighting image with a weighting value greater than a prespecified weight threshold value.

3. The method as claimed in claim 1, characterized in that, to generate the first and the second weighting images from the anatomical image or from the object image, first a respective binary image is generated in that a first binary value is assigned to pixels belonging to the anatomical feature or to the instrument and a second binary value is assigned to the respective remaining pixels and then the first weighting value is assigned to the pixels with the first binary value.

4. The method as claimed in claim 1, characterized in that a respective safety region is defined, which adjoins and surrounds the pixels belonging to the anatomical feature or to the instrument, and these safety regions are assigned the same weighting value as the pixels belonging to the anatomical feature or to the instrument.

5. The method as claimed in claim 1, characterized in that a nonlinear function is used as the prespecified monotonously decreasing function.

6. The method as claimed in claim 5, characterized in that the nonlinear function comprises an exponential function or a polynomial function.

7. The method as claimed in claim 1, characterized in that a sequence of a plurality of the object images is generated and provided, wherein in each case, an updated first weighting image is generated not for all images of this plurality of object images but only for images selected in accordance with a prespecified selection rule.

8. The method as claimed in claim 7, characterized in that the selection uses the prespecified selection rule comprising only for each n-th image of the plurality of object images, wherein n indicates a prespecified number.

9. The method as claimed in claim 1, further comprising:
generating a plurality of object images,
generating a respective difference image in that a previously generated image of the plurality of object images is subtracted from at least one image of the plurality of object images,
generating a respective difference weighting image from the difference image in that a first difference weighting value is allocated to pixels belonging to the instrument and a second difference weighting value, which is smaller than the first difference weighting value, is assigned to the remaining image regions, and
in generating the overall weighting image, the first and the second weighting image and the difference weighting image are combined with one another.

10. A non-transitory computer readable memory for a control apparatus of an imaging apparatus, wherein a program code at least comprising a computer program is stored therein, the program code comprising instructions for:
provision of an anatomical image depicting a prespecified segmented anatomical feature of a target object,
provision of an object image depicting a segmented instrument in a region of the target object, wherein a recording region of the object image corresponds to a recording region of the anatomical image,
generation of a first weighting image from the anatomical image and a second weighting image from the object image in that a prespecified first weighting value is assigned in each case to pixels belonging to the anatomical feature or to pixels belonging to the instrument, in each case pixels at an edge of the recording region that do not belong to the anatomical feature or do not belong to the instrument are assigned a prespecified second weighting value that is smaller than the first weighting value, and intermediate pixels are assigned a weighting value between the first and the second weighting values according to a prespecified monotonously decreasing function in dependence on a location of the respective pixel in the recording region,
generation of an overall weighting image from combination of the first and the second weighting images with one another, and
provision of the overall weighting image and/or a region of interest determined using the overall weighting image as input data for an image processing algorithm,
wherein the image processing algorithm is a pixel-shift algorithm, which registers the object image to the anatomical image for overlaying and, for this purpose, compensates a movement of the target object and/or the imaging apparatus between respective acquisition time points of the anatomical image and the object image taking account of the overall weighting image, and
wherein image regions that are allocated a relatively higher weighting value by the overall weighting image are prioritized for a greater registration accuracy in motion compensation by the pixel-shift algorithm over other image regions allocated a relatively lower weighting value and a relatively lesser registration accuracy.

11. The non-transitory computer readable memory of claim 10 wherein the instructions are characterized in that the region of interest in the anatomical image and in the object image is determined as the respective image regions thereof corresponding to the pixels of the overall weighting image with a weighting value greater than a prespecified weight threshold value.

12. The non-transitory computer readable memory of claim 11 wherein the instructions are characterized in that, to generate the first and the second weighting images from the anatomical image or from the object image, first a respective binary image is generated in that a first binary value is assigned to pixels belonging to the anatomical feature or to the instrument and a second binary value is assigned to the respective remaining pixels and then the first weighting value is assigned to the pixels with the first binary value.

13. An imaging apparatus for roadmap imaging, the imaging apparatus comprising:
an acquisition facility for acquiring images of a target object;
a control apparatus; and
a data memory storing instructions for the control apparatus, where the control apparatus executing the instructions is configured to:
provide an anatomical image depicting a prespecified segmented anatomical feature of the target object,
provide an object image depicting a segmented instrument in a region of the target object, wherein a recording region of the object image corresponds to a recording region of the anatomical image,
generate a first weighting image from the anatomical image and a second weighting image from the object image in that a prespecified first weighting value is assigned in each case to pixels belonging to the anatomical feature or to pixels belonging to the instrument, in each case pixels at an edge of the recording region that do not belong to the anatomical feature or do not belong to the instrument are assigned a prespecified second weighting value that is smaller than the first weighting value, and intermediate pixels are assigned a weighting value between the first and the second weighting values according to a prespecified monotonously decreasing function in dependence on a location of the respective pixel in the recording region,
generate an overall weighting image from combination of the first and the second weighting images with one another, and provide the overall weighting image and/or a region of interest determined using the overall weighting image as input data for an image processing algorithm, wherein the image processing algorithm is a pixel-shift algorithm, which registers the object image to the anatomical image for overlaying and, for this purpose, compensates a movement of the target object and/or the imaging apparatus between respective acquisition time points of the anatomical image and the object image taking account of the overall weighting image, and wherein image regions that are allocated a relatively higher weighting value by the overall weighting image are prioritized for a greater registration accuracy in motion compensation by the pixel-shift algorithm over other image regions allocated a relatively lower weighting value and a relatively lesser registration accuracy.

14. The imaging apparatus of claim 13 wherein the instructions are characterized in that the region of interest in the anatomical image and in the object image is determined as the respective image regions thereof corresponding to the pixels of the overall weighting image with a weighting value greater than a prespecified weight threshold value.

15. The imaging apparatus of claim 14 wherein the instructions are characterized in that, to generate the first and the second weighting images from the anatomical image or from the object image, first a respective binary image is generated in that a first binary value is assigned to pixels belonging to the anatomical feature or to the instrument and a second binary value is assigned to the respective remaining pixels and then the first weighting value is assigned to the pixels with the first binary value.

* * * * *